(12) United States Patent  (10) Patent No.: US 7,120,504 B2
Osypka  (45) Date of Patent: Oct. 10, 2006

(54) EPICARDIAL SCREW-IN LEAD

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 526 days.

(21) Appl. No.: 10/625,175

(22) Filed: Jul. 23, 2003

(65) Prior Publication Data

US 2004/0127967 A1  Jul. 1, 2004

Related U.S. Application Data

(60) Provisional application No. 60/427,983, filed on Nov. 19, 2002, provisional application No. 60/398,677, filed on Jul. 25, 2002.

(51) Int. Cl.
*A61N 1/05* (2006.01)
(52) U.S. Cl. .................................... 607/131
(58) Field of Classification Search ................ 607/121, 607/131
See application file for complete search history.

(56) References Cited

U.S. PATENT DOCUMENTS

| 4,010,758 | A |   | 3/1977  | Rockland et al. |         |
|-----------|---|---|---------|-----------------|---------|
| 4,235,246 | A |   | 11/1980 | Weiss           |         |
| 4,299,239 | A | * | 11/1981 | Weiss et al.    | 607/131 |
| 4,357,946 | A | * | 11/1982 | Dutcher et al.  | 607/131 |
| 4,953,564 | A | * | 9/1990  | Berthelsen      | 607/120 |
| 4,972,847 | A |   | 11/1990 | Dutcher et al.  |         |
| 5,143,090 | A |   | 9/1992  | Dutcher et al.  |         |
| 5,217,028 | A |   | 6/1993  | Dutcher et al.  |         |
| 5,255,693 | A |   | 10/1993 | Dutcher et al.  |         |
| 5,300,107 | A |   | 4/1994  | Stokes et al.   |         |
| 5,374,287 | A | * | 12/1994 | Rubin           | 607/131 |
| 5,531,780 | A | * | 7/1996  | Vachon          | 607/120 |
| 5,545,201 | A | * | 8/1996  | Helland et al.  | 607/127 |
| 5,575,814 | A |   | 11/1996 | Giele et al.    |         |
| 5,697,964 | A | * | 12/1997 | Gates           | 607/122 |
| 6,819,959 | B1| * | 11/2004 | Doan et al.     | 607/127 |

OTHER PUBLICATIONS

International Search Report dated Dec. 29, 2003.

* cited by examiner

*Primary Examiner*—George Manuel
(74) *Attorney, Agent, or Firm*—Scott D. Wofsy; Edwards Angell Palmer & Dodge LLP

(57) ABSTRACT

An epicardial screw-in lead is disclosed which includes an elongated lead body, an electrode housing at a distal end of the lead body for stimulating cardiac tissue, and a helical fixation screw within the electrode housing which can be extended to affix the electrode housing to the cardiac tissue. Preferably at least a portion of the helical fixation screw is electrically active. A lead implantation kit is also disclosed that can include the screw-in lead, a screwdriver tipped stylet for activating the screw, and a flexible guiding sheath for directing the tip of the stylet to the electrode housing.

47 Claims, 6 Drawing Sheets

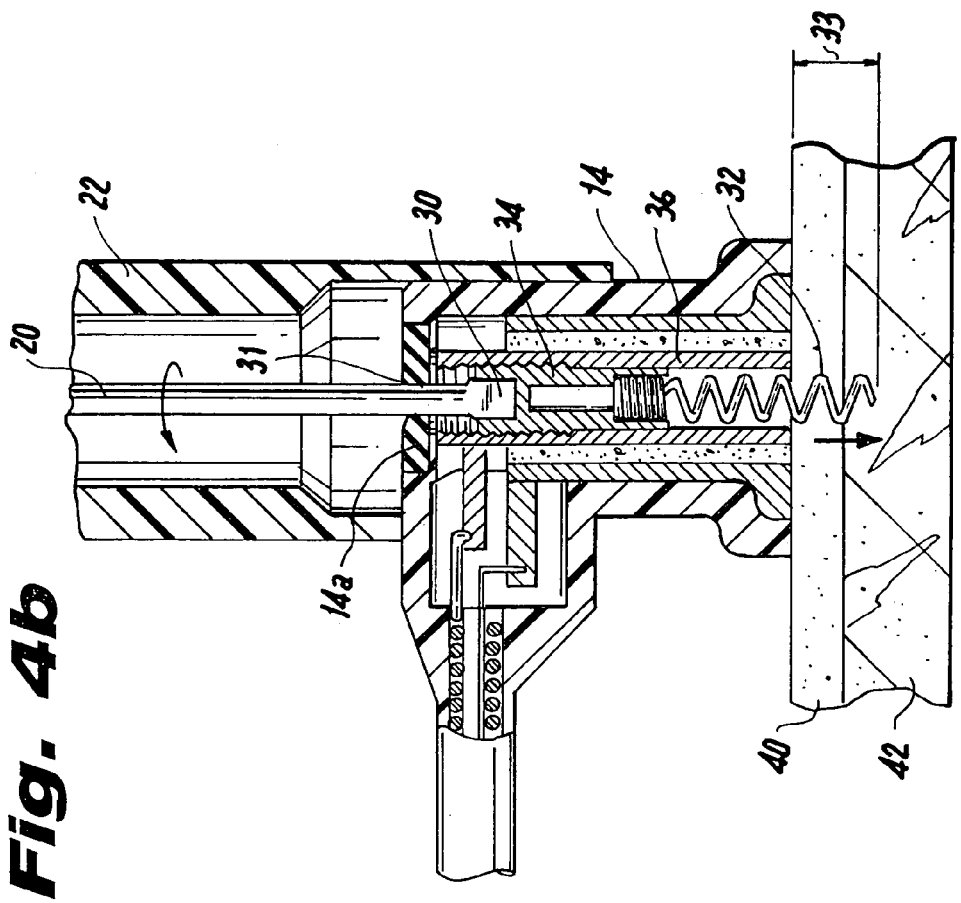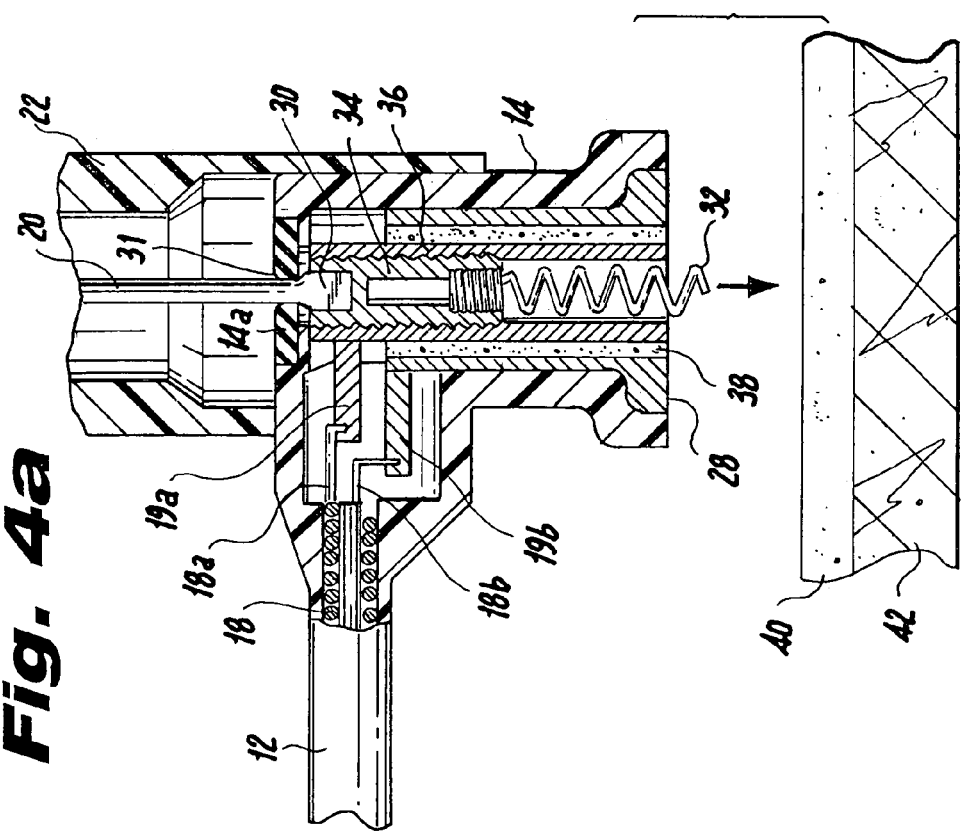

EPICARDIAL SCREW-IN LEAD

CROSS-REFERENCE TO RELATED APPLICATIONS

The subject application claims priority to U.S. Provisional Application Ser. No. 60/398,677, filed on Jul. 25, 2002, and U.S. Provisional Application Ser. No. 60/427,983, filed on Nov. 19, 2002, the disclosures of which are herein incorporated by reference in their entireties.

BACKGROUND OF THE INVENTION

1. Field of the Invention

The subject invention relates to an epicardial implantable screw-in lead, and more particularly, to an epicardial pacing lead for left ventricular placement to effect bi-ventricular pacing of the heart.

2. Background of the Related Art

Implantable cardiac stimulation leads, including endocardial leads, are well known in the art. In general, these devices have an elongated flexible body with an electrode at one end for contacting cardiac tissue and a connector at the other end for mating with an automated stimulation device, namely a pacemaker.

Epicardial implantable pacing leads currently in use are amenable to flexible placement outside the heart, i.e., the left ventricle easily can be reached from the outside. However, the placement of epicardial leads into the myocardium often requires open heart surgery. Another disadvantage of placing leads epicardially is the increased pacing threshold caused by the fatty tissue layer outside the myocardium. Such increased threshold reduces the battery life of the pacemaker, creating the need for more frequent replacement of the battery or the pacemaker itself.

Pacing threshold is lowered when leads are placed endocardially. Another advantage of such placement of the leads, particularly when used in the coronary sinus or left ventricle for bi-ventricular pacing (resynchronization), is that it does not require open heart surgery. A particularly useful coronary sinus lead is disclosed in U.S. Patent Application Publication US 2003/0023295. However, the anatomy of the coronary sinus makes endocardial placement of the leads very difficult. In addition, endocardial left ventricular placement (transseptal approach from the right atrium) can be dangerous for patients, since any blood that arises could go directly into the blood circulation of the brain. Furthermore, transseptal approach requires a hole to be punctured into the septum to reach the left ventricle towards the left atrium. This could cause severe trauma to the patient.

When an endocardial lead has been implanted in the heart, either by active or passive fixation, it has been determined that the cardiac tissue at the site of implantation will react favorably to the lead in the presence of a therapeutic drug, for example, a steroid. Consequently, cardiac leads have been designed with means for delivering a therapeutic drug to the cardiac tissue at the implantation site. A particularly useful drug delivery device is disclosed in U.S. Patent Application Publication US 2003/0093138, the disclosure of which is incorporated by reference into the subject application. This device includes an insulating tube 26 that is formed from a compound that includes an elastomeric material and a therapeutic drug. In use, suitable drugs such as steroids elute from the elastomer over time, having a desirable effect on surrounding cardiac tissue. A distal end of the lead body is provided with a plurality of flexible tines to keep the lead tip firmly anchored within the cardiac tissue.

An example of a myocardial pacing lead is disclosed in U.S. Pat. No. 5,300,107, wherein an electrode 9 and a portion of the lead body penetrate the epicardium for direct stimulation of the myocardium. The lead includes two sets of opposing tines 3 and 7, the first row of tines 3 anchoring on the inside wall of the epicardium, and the second row of tines 7 preventing excessive penetration into the myocardium, thereby maintaining the electrode 9 in contact with the myocardium.

Another type of pacing lead is disclosed in U.S. Pat. No. 4,357,946, in which an epicardial pacing lead stylet is used to control a helical fixation screw which is rotated to engage the epicardial tissue of the heart. The stylet 30 is threaded through the lead, which is formed of a multifilar insulated coiled conductor, and configured such that a wedged tip 30b of the stylet 30 engages a complex gear set 50. The wedged tip 30b rotates the gear set 50, which drives the helical fixation screw 42 into the epicardial tissue. At fixation, a ring electrode 38 rests against epicardial tissue, the electrode being secured to the pacing site by the helical fixation screw 42. In the '946 patent, electrical stimulation is applied exclusively through the ring electrode 38; no electrical stimulation is effected through the helical fixation screw itself. Moreover, control of the screw is effected through a complex gear arrangement, and further requires a rotatable stylet to be internally threaded through the coiled conductor of the lead to transmit torque to the gears.

It would be beneficial to provide an epicardial screw-in lead that overcomes the deficiencies of the prior art. More particularly, it would be beneficial to provide an epicardial screw-in lead in which electrical stimulation is incorporated into the lead's fixation mechanism. Moreover, control of the screw preferably is provided in a simplified arrangement, while permitting the stylet to be positioned outside the lead.

SUMMARY OF THE INVENTION

The subject invention is directed to a new and useful bipolar epicardial implantable screw-in lead. The lead includes an elongated flexible body formed from a biocompatible insulative material and having opposed proximal and distal end portions. A conventional lead connector is operatively associated with the proximal end portion of the lead body for connection to a pacemaker, pulse generator, or other electrical stimulation device. The lead body preferably includes an interior lumen adapted to receive at least one stranded wire conductor or at least one conductor coil, e.g., a multifilar conductor coil with up to eight filaments, which is electrically connected to portions of an electrode housing. The electrode housing preferably includes a ring electrode operatively associated with the distal end portion of the lead body. A helical fixation screw is coaxially disposed within the ring electrode, the screw serving as a fixation mechanism for affixing the electrode housing to cardiac tissue. The screw can be extended and retracted from the epicardium and/or myocardium.

An insulating member (insulating tube) preferably is disposed within an annular gap formed between the fixation screw and the ring electrode for electrically isolating the ring electrode from the fixation screw. The insulating tube also serves as a drug elution device. Preferably the insulating tube includes about 15% to 25% by weight anti-inflammatory drug. In one embodiment, the drug eluting insulating tube can be formed from a silicone rubber and a steroid.

Preferably, the composition is cut into rings having a durometer of about 20 to 90 Shore A, more preferably about 40 to 90 Shore A.

The delivery of the epicardial screw-in lead of the subject invention to the left venticle can be effected inside a positioning tube (endoscope) through the fourth intercostal space. The fixation screw in all described configurations can be extended/retracted using a fixation tool (e.g. screwdriver shaped stylet or connector pin activation [Bisping type]). After the distal tip of the lead is fixed inside the myocardium, the lead body can be tunneled subcutaneously to the pacemaker pouch.

The helical fixation screw depends from an externally threaded plug supported within an internally threaded collar disposed within the electrode housing. The plug is configured for engagement with the screwdriver tipped stylet which is received in the electrode housing. Preferably the screwdriver tipped stylet is positioned outside the lead body, in a guiding sheath, so that the lead body remains flexible for easy manipulation and positioning.

The helical fixation screw includes a proximal portion and a distal portion terminating in a tip portion, the tip portion being an electrically active portion. One or more other electrically active portions also can be provided on the screw. In one embodiment, the ring electrode serves as an anode, and the tip portion serves as a cathode. In another embodiment, the ring electrode and the proximal portion of the screw serves as an anode, and the tip portion of the screw serves as a cathode. Preferably an insulator is provided to electrically insulate the tip portion from the proximal portion of the screw.

The subject invention is directed to a bipolar cardiac lead and a cardiac lead implantation kit incorporating the above-described cardiac lead. The cardiac lead implantation kit can include the bipolar cardiac lead (e.g., including an elongated lead body, an electrode housing operatively associated with a distal end portion of the lead body, and a helical fixation screw disposed within the electrode housing), a screwdriver tipped stylet for facilitating movement of the helical fixation screw, and a flexible guide sheath for directing the tip of the stylet to the electrode housing.

These and other unique features of the epicardial screw-in lead and cardiac lead implantation kit of the subject invention will become more readily apparent from the following description of the drawings taken in conjunction with the detailed description of the preferred embodiments.

BRIEF DESCRIPTION OF THE DRAWINGS

So that those having ordinary skill in the art to which the subject invention appertains will more readily understand how to construct and use epicardial implantable screw-in leads of the subject invention, reference may be had to the drawings wherein:

FIG. 4a is a side elevational view in cross-section of the electrode housing and helical fixation screw of the lead shown in FIG. 1 in an axially retracted position prior to placement within coronary tissue;

FIG. 4b is a side elevational view in cross-section of the electrode housing and helical fixation screw of FIG. 4a in an axially extended position implanted within epicardial tissue;

These and other features of the epicardial screw-in lead and cardiac lead implantation kit of the subject invention will become more readily apparent to those having ordinary skill in the art from the following detailed description of the preferred embodiments.

DETAILED DESCRIPTION OF THE PREFERRED EMBODIMENTS

In the description which follows, the term "proximal" refers to the end of the epicardial screw-in lead which is farthest from the surgical site, while the term "distal" refers to the end of the device which is nearest to the surgical site.

Figure 1:
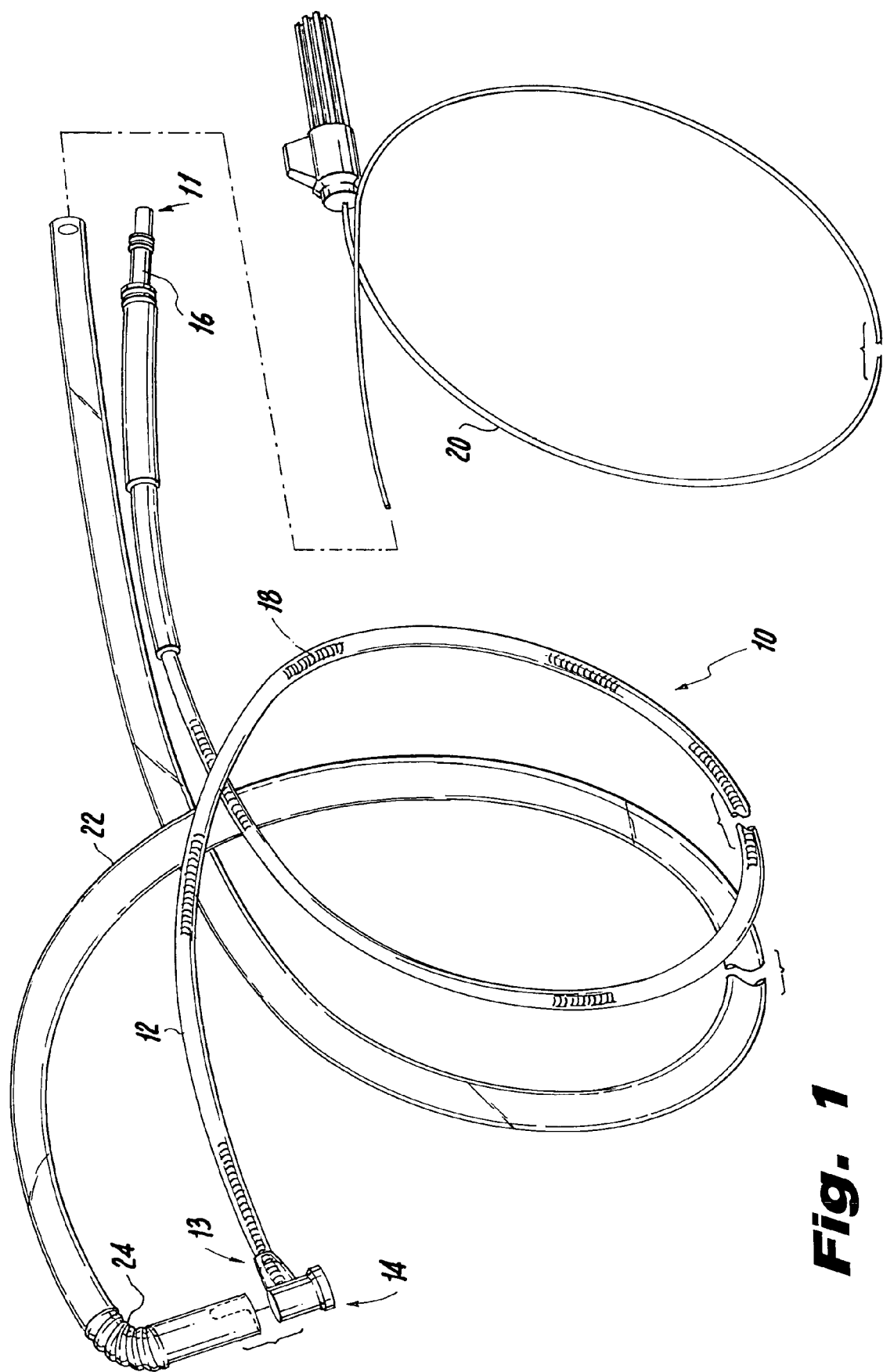
FIG. 1 is a perspective view of an epicardial screw-in lead and a guiding sheath for receiving a stylet, which are constructed in accordance with a preferred embodiment of the subject invention.

Referring now to the drawings wherein like reference numerals identify similar aspects of the subject invention, a bipolar epicardial implantable screw-in lead is disclosed in FIGS. 1 through 8, the screw-in lead being particularly useful for left ventricular placement to effect bi-ventricular pacing of the heart. With particular reference to FIG. 1, the epicardial screw-in lead 10 of the subject invention has an elongated flexible lead body 12 having a proximal end portion 11 and an opposed distal end portion 13. The lead body 12 is formed from a bio-compatible insulative material such as silicone rubber, polyurethane, or the like.

With continuing reference to FIG. 1, a bipolar electrode housing 14 is operatively associated with the distal end portion 13 of the elongated lead body 12 for stimulating cardiac tissue. A connector 16 is operatively associated with the proximal end 11 of the elongated lead body 12 for communicating with a corresponding adapter associated with a pulse generator or pacemaker (not shown). The connector 16 may be of any standard type, size, or configuration such as, for example, a bipolar IS-1 type connector (International Standard ISO 5841.3:1992).

Connector 16 is electrically connected to the electrode housing 14 by way of at least one conductor coil 18 that extends through an interior lumen of lead body 12. Preferably, conductor coil 18 is generally helical in configuration and includes one or more conductive wires or filaments. For example, the conductor coil 18 may be a multifilar conductor coil with as many as eight (8) filaments. Other conductors may be employed such as flexible low-ohm DFT drawn filled rope tubing. The structure and function of conductor coil 18 and its elements are generally known. A particularly useful multifilar coil is disclosed in U.S. Patent Application Publication US 2003/0092303, which is incorporated by reference into the subject application.

A flexible guiding sheath 22 is provided for guiding a stylet 20, the stylet being adapted to drive a screw at a distal end of the electrode assembly 14. Preferably, the stylet 20 is a relatively thin, rigid stylet that is received in an interior passage of the flexible guiding sheath 22. The guiding sheath 22 can be made from a bendable or flexible material, which is preferably bio-compatible (e.g., polyurethane, nylon, polyamide or the like). The guiding sheath 22 can be peelable or splittable, and preferably includes one or more accordion-like sections such as bendable section 24 to enable flexible positioning of the guiding sheath 22.

In the subject invention, the stylet 20 is received in the guiding sheath 22, instead of being accommodated within the interior lumen of the lead body 12. Accordingly, the lead body 12 maintains flexibility for easy manipulation and positioning, thereby permitting placement of the electrode housing 14 in relatively inaccessible or difficult to access sections of the epicardium. This can be particularly helpful if the lead is used for left ventricular pacing, or if the lead must be positioned behind the heart without open heart surgery, e.g., as required in minimally invasive surgery. In prior art devices, the rigid stylet typically is threaded through the lead body, thereby conferring rigidity to the lead body, and restricting its flexibility and movement.

Figure 2:
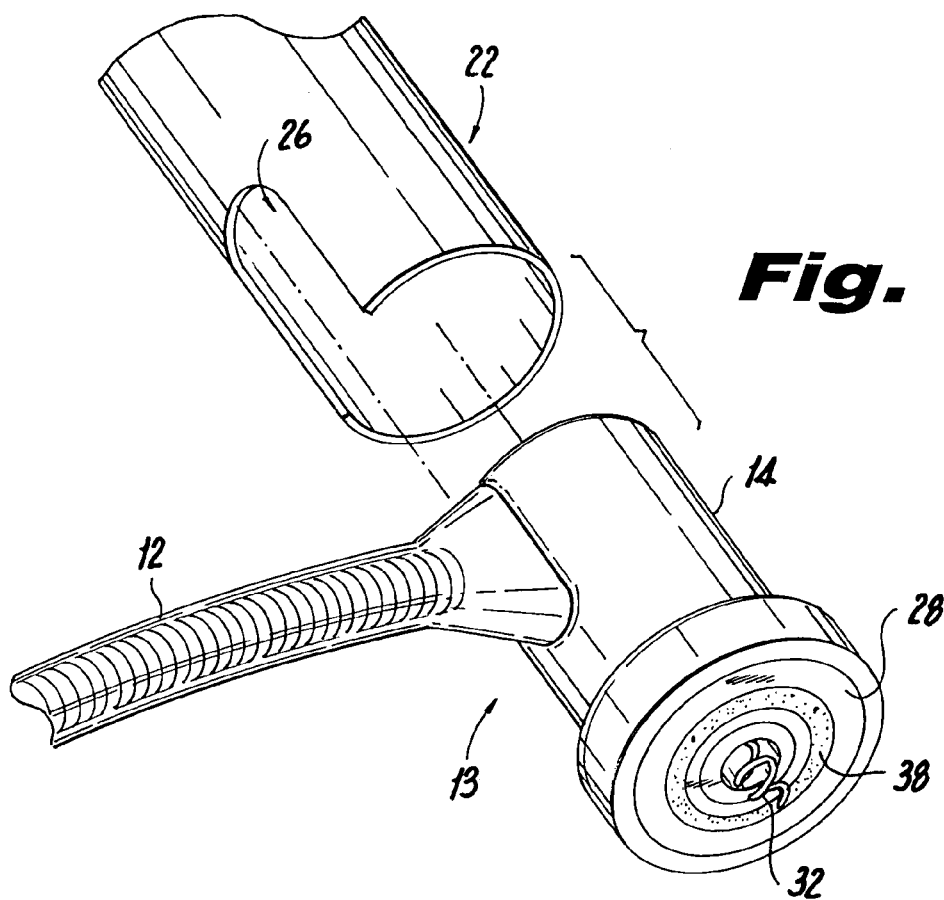
FIG. 2 is an enlarged perspective view of the distal end portions of the lead and guiding sheath shown in FIG. 1, with the two structures separated from each other for ease of illustration.
Figure 3:
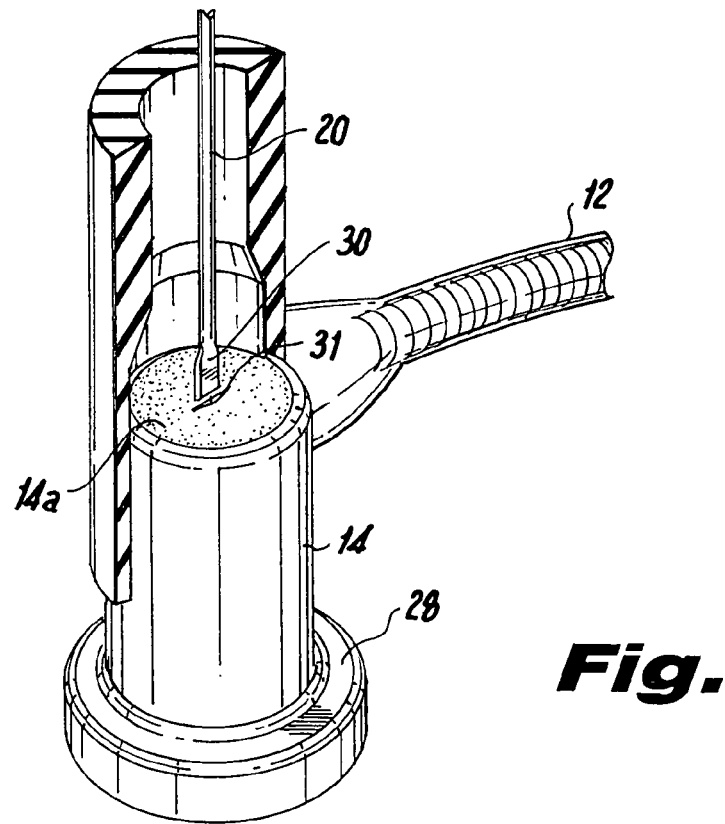
FIG. 3 is an enlarged perspective view in partial cross-section of the screwdriver tipped stylet as received in the electrode housing of the lead shown in FIG. 1.

With reference to FIGS. 2 and 3, the guiding sheath 22 preferably includes a cut-out section 26, which is configured and arranged for receiving the distal end portion 13 of the lead body 12, thereby enabling frictional engagement between the guiding sheath 22 and the lead body 12. The interior passage of the guiding sheath 22, which also receives the stylet 20, preferably terminates in a self-sealing opening in proximity of the cut-out section 26. More preferably, a self-sealing seal (not shown) made of silicon or like material can be provided to seal the opening of the guiding sheath passage.

The stylet 20, preferably received in the guiding sheath 22, terminates in a screwdriver-shaped flat tip 30. The tip 30 is configured and arranged to be received in a self-sealing opening or slot 31 formed in the electrode housing 14. The upper surface portion 14a of the electrode housing 14 in which the opening or slot 31 is formed, is preferably constructed from an elastomer such as, for example, silicone or a similar material. The self-sealing opening can be provided as a single cut or slit, or it can be in the form of a self-sealing tricuspid-shaped opening similar to that which is defined by a conventional trocar seal, or it can be in the form of a self-sealing duckbill-type opening. Engagement of the stylet, and specifically the tip 30, within the electrode housing 14 is discussed in further detail below with reference to FIGS. 4a and 4b.

The electrode housing 14 is adapted and configured to provide a relatively high impedance pacing surface for stimulating cardiac tissue. Electrode housing 14 includes a radially outer anodic ring electrode 28, located at approximately the distal end 13 of the lead body 12. An extendible/retractable helical fixation screw 32 preferably is positioned radially inside the ring electrode 28, the helical fixation screw serving as a fixation mechanism for affixing the electrode housing 14 to the cardiac tissue, e.g., the epicardium and/or myocardium. The ring electrode 28 and helical fixation screw 32 preferably are coated with or formed from platinum, stainless steel MP35N, a platinum-iridium alloy or a similar bio-compatible metallic material.

As shown in FIGS. 4a and 4b, the stylet 20 with tip 30 defines an axis which extends generally perpendicular to a longitudinal axis of the lead body 12. Upon insertion of the stylet tip 30 through the self-sealing slot 31 and into the electrode housing 14, the tip 30 preferably engages with an externally threaded plug 34. The plug 34 preferably includes a proximal end for receiving the screwdriver tipped stylet, such as the flat head of the stylet tip 30, and a distal end for receiving the helical fixation screw 32. The plug 34 is adapted for engagement within an internally threaded collar 36 positioned radially inside the ring electrode 28 of the electrode housing 14. Preferably the internal threads of the collar 36 are configured for engagement with external threads of the plug 34. An annular gap is formed between the inner periphery of the ring electrode 28 and the outer periphery of the collar 36.

Electrical connections can be made between the conductor coil 18 and the above-described elements of the electrode housing 14. As discussed above, preferably the conductor coil 18 includes a plurality of filaments or elements which are wound together in the coil, the elements carrying electricity to the electrode housing 14. As shown in FIG. 4a, element 18a is electrically connected to the collar 36 via connector 19a, thereby delivering a negative charge to one or more portions of fixation screw 32, such as through connection between the collar 36, plug 34, and screw 32. It is also within the scope of the invention to deliver a positive charge to the screw, or both positive and negative charges to different portions of the screw. Element 18b of the conductor coil is electrically connected to the ring electrode 28 via connector 19b and carries a positive charge, thereby imparting a positive charge to the anodic ring electrode 28. The elements 18a and 18b and electrical connectors 19a and 19b are merely examples of electrical connections that can be made between the conductor coil 18 and various components of the electrode housing 14, and it is within the scope of the subject invention to provide more or fewer electrical connections.

An elastomeric insulating tube 38 is firmly disposed within the annular gap between the ring electrode 28 and the collar 36 for electrically isolating the ring electrode 28 from the collar 36 and helical fixation screw 32. The insulating tube 38 preferably also serves as a drug elution device. More particularly, the insulating tube 38 can be formed from a compound that includes an elastomeric material and a therapeutic drug. In use, the drug elutes from the elastomer over time, having a desirable effect on surrounding cardiac tissue. Suitable drugs include anti-inflammatory drugs such as steroids, including for example, dexamethasone sodium phosphate and dexamethasone sodium acetate. Such steroids control inflammation in the tissue located at the implantation site of the lead. Other steroids and non-steroidal based drugs may also be used. In an embodiment of the subject invention, the drug eluting insulating tube 38 includes about 15% to 25% by weight anti-inflammatory drug.

In an embodiment of the subject invention, insulating tube 38 is formed by mixing silicone rubber together with the steroid. The composition is then extruded or molded into a tubular form and subsequently cut into rings having a desired length and a durometer of about 20 to 90 Shore A, preferably about 40 to 90 Shore A. It has been recognized that a ring having a durometer of approximately 40 to 60 Shore A provides for a particularly fast elution rate. Alternatively, the composition may be used to mold tubes of a desired length. In either instance, after formation, the tubes are glued in place using a silicone adhesive.

The length of the helical fixation screw 32 according to the subject invention preferably is longer than that of the fixation screws currently in use, the helical fixation screw 32 preferably having a penetration range 33 of about 3 mm to 10 mm, more preferably up to about 8 mm (see FIG. 4b). This allows the fixation screw to be screwed into the myocardium 42 until the fatty tissue layer 40 surrounding the heart is pierced and the excitable cardiac tissue is reached for effective and low threshold pacing.

FIG. 4a depicts a first state of the helical fixation screw 32, in which the screw 32 is in an axially retracted position prior to placement of the screw within the coronary tissue; FIG. 4b depicts a second state in which the helical fixation screw 32 is implanted in the epicardium and being driven toward an axially extended position. The stylet 20 controls the helical fixation screw 32 positioned in the electrode housing 14 of the pacing lead, in that the stylet 20 is turned (e.g., by external rotation of the stylet), thereby advancing the helical fixation screw 32 beyond the planar surface of the electrode ring 28. In FIGS. 4a and 4b, the stylet tip 30 has been inserted in the plug 34, which by threaded engagement between the plug 34 and collar 36 causes the collar to rotate, resulting in rotation of the helical fixation screw 32. As shown in FIG. 4b, the helical fixation screw 32 can be driven through the fatty tissue layer 40 into the myocardium 42. Once the helical fixation screw 32 is extended in the myocardium 42, and the planar surface of the ring electrode 28 is positioned, thresholds can be measured, the stylet 20 and guiding sheath 22 can be retracted, and the lead body 12 can be tunneled toward the implantable pulse generator (not shown). Depending on the measured thresholds, the helical fixation screw 32 can be extended to a penetration range 33 of about 3 mm to 10 mm, more preferably up to about 8 mm.

Figure 5:
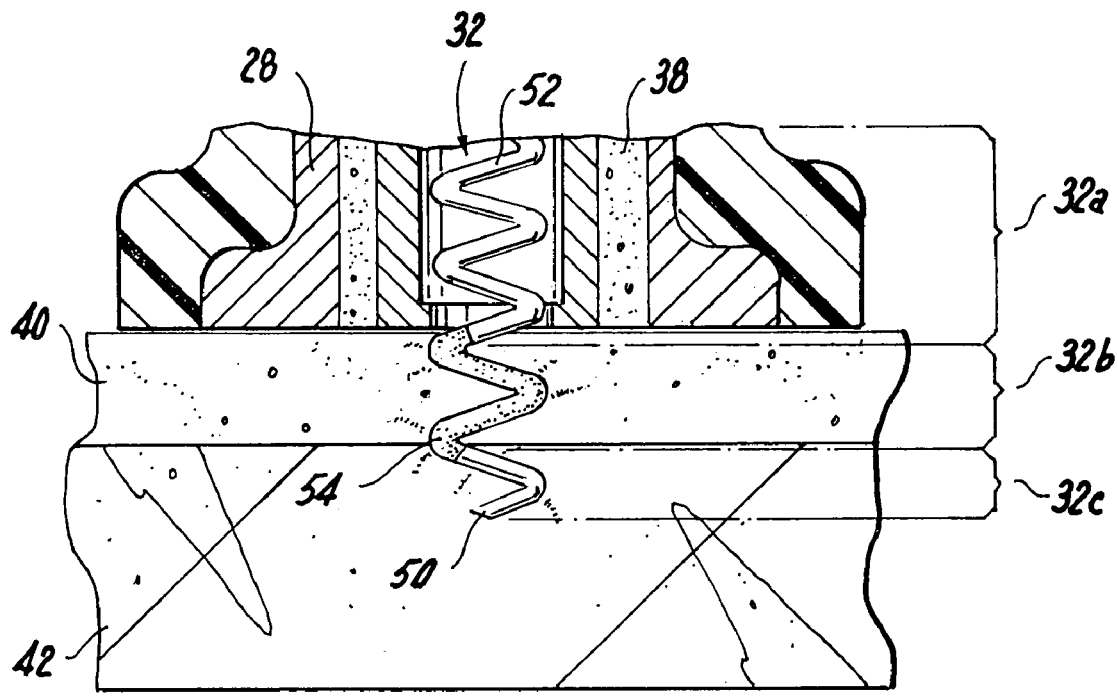
FIG. 5 is an enlarged cross-sectional view of the screw-in lead shown in FIG. 1, wherein an electrically active layer on the proximal portion of the helical fixation screw and the electrode ring around the screw serve as an anode, and an electrically active layer on the tip portion of the screw serves as a cathode.

According to one embodiment of the subject invention, as depicted in FIG. 5, the helical fixation screw 32 has a proximal portion 32a and a distal portion 32b terminating in a tip portion 32c. The tip portion 32c of the screw preferably includes an electrically active portion 50, which can serve as a cathode, and the proximal portion 32a has an electrically active portion 52, which can serve as an anode and which is insulated from the cathode portion 50 by an insulator 54. The insulator 54 can be constructed from a nonconductive biocompatible material, such as Teflon®, polyimide, polyamide (Nylon), Parylene®, polyurethane or other similar material. For example, the insulator 54 can be formed as an additional layer over one or more portions of the helical fixation screw 32. In the embodiment shown in FIG. 5, the electrode ring 28 positioned around the helical fixation screw 32 preferably also serves as an anode. In this embodiment, the tip portion 32c of the helical fixation screw 32 serves as the cathode, and the electrically active portions of the electrode ring 28 and the tip portion 32c are insulated from one another by the elastomeric insulating tube 38. Alternatively, the anode may include both the proximal portion 32a of the screw and the electrode ring 28. It will also be understood by those of ordinary skill in the art that electrically active portions 50 and 52 may be located anywhere on the helical fixation screw 32, and their polarity may be reversed.

Figure 6:
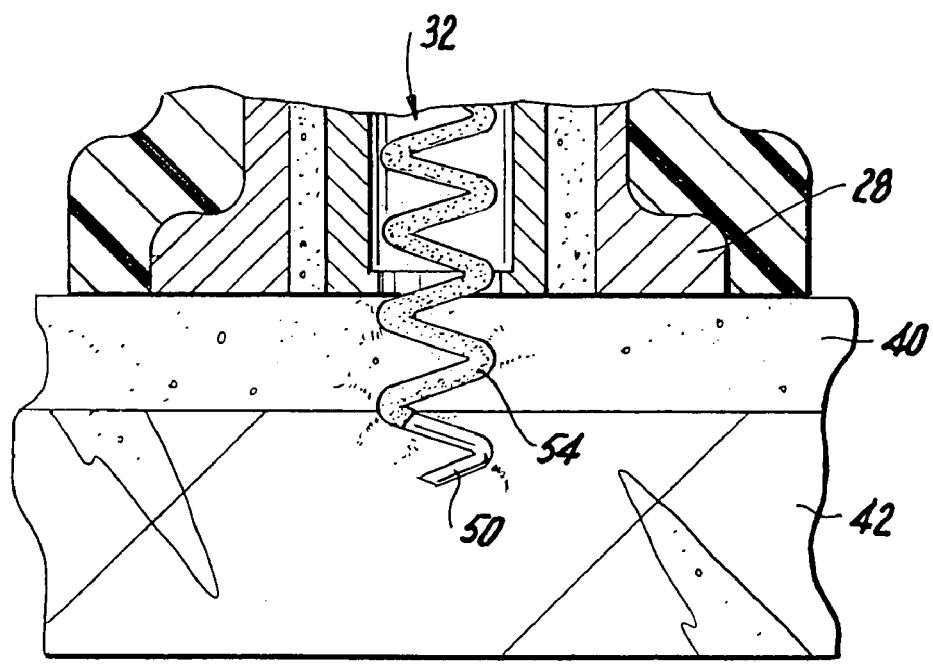
FIG. 6 also is an enlarged cross-sectional view of the screw-in lead shown in FIG. 1, wherein the electrode ring around the helical fixation screw alone serves as an anode, and an electrically active layer on the tip portion of the screw serves as a cathode.

FIG. 6 depicts another embodiment of the subject invention, in which the tip portion 32c of the screw includes electrically active portion 50 which serves as a cathode, and both the proximal and distal portions of the screw 32 are covered by insulator 54. In this embodiment, electrically active portion 50 covers only the tip portion 32c, and the electrode ring 28 alone serves as an anode.

Figure 7:
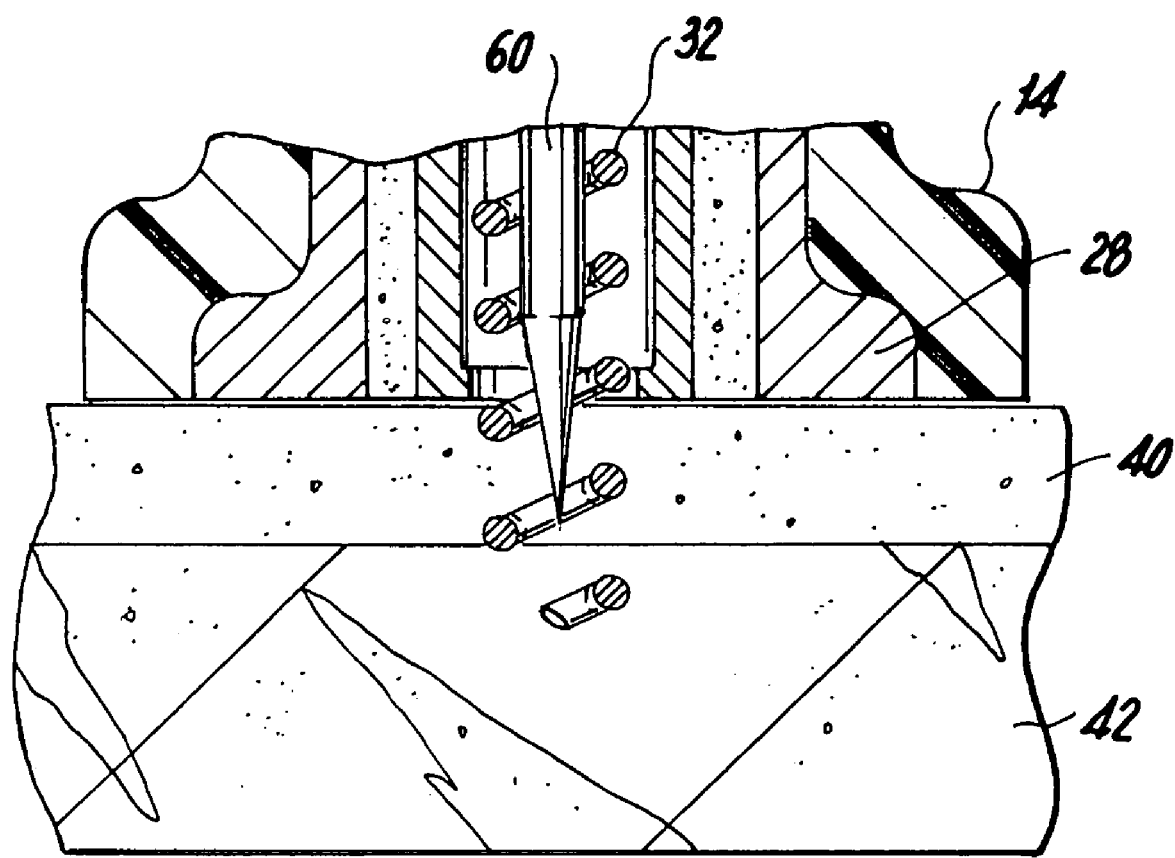
FIG. 7 is an enlarged cross-sectional view of the screw-in lead according to the present invention, wherein the extendible/retractable helical fixation screw serves as an anode, and a fixed needle-shaped fixation pin positioned inside the screw serves as a cathode.

According to yet another embodiment of the subject invention, shown in FIG. 7, the electrode housing 14 encloses ring electrode 28, extendible/retractable fixation screw 32, and a fixed needle-shaped fixation pin 60 positioned within the helical fixation screw 32. The fixation screw 32 can be electrically active as an anode and the pin 60 can be electrically active as a cathode, or vice versa. The length of the screw 32 according to this embodiment is preferably about 7 to 10 mm, and its diameter is preferably about 5 mm. The length of the pin 60 is preferably about 5 to 7 mm. According to one configuration of this embodiment, the fixation pin 60 is concentrical with the fixation screw 32. However, other configurations are included within the scope of the subject invention, such as where the pin is off-centered, so long as the electrical elements of different polarities are insulated from one another.

Figure 8:
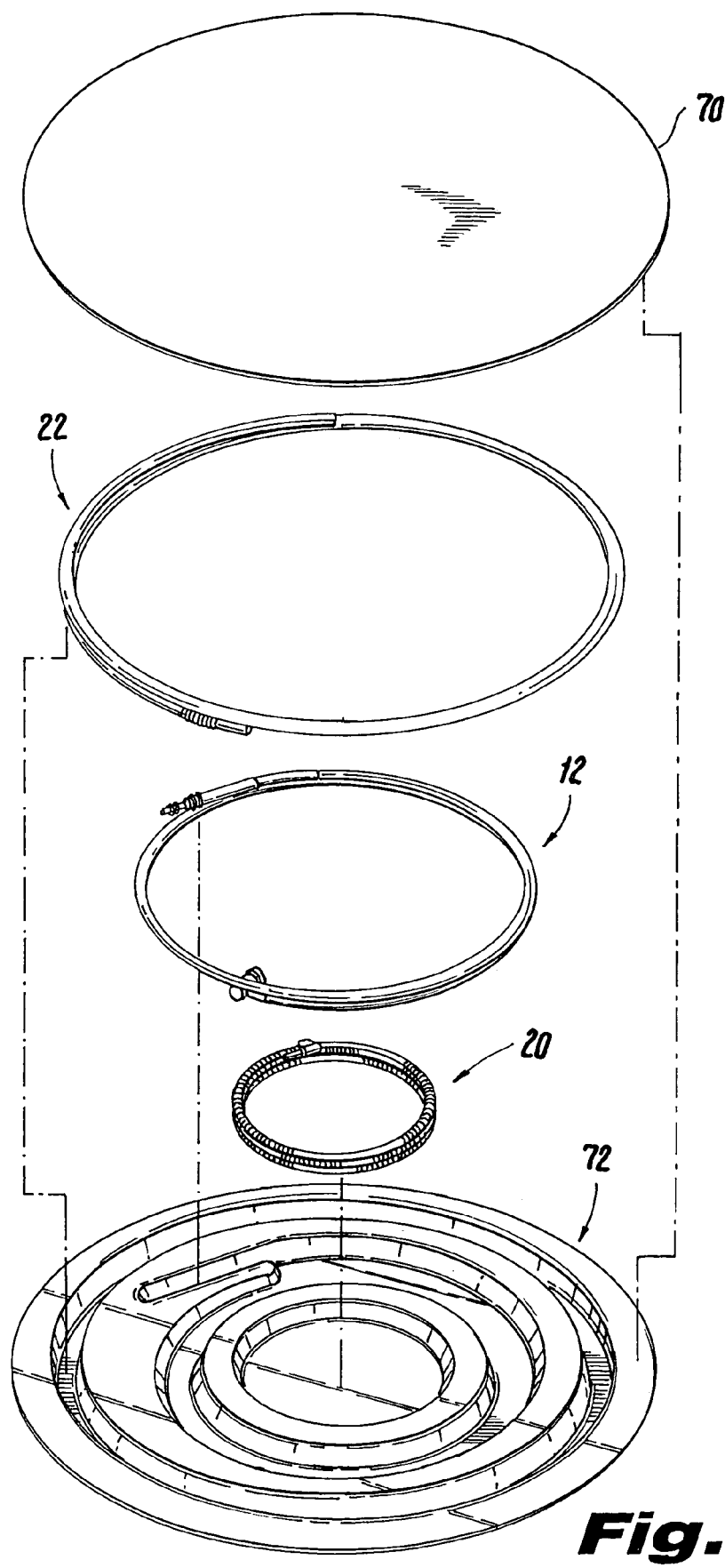
FIG. 8 is a perspective view illustrating the components of a cardiac lead implantation kit according to a preferred embodiment of the subject invention.

FIG. 8 depicts a cardiac lead implantation kit according to the subject invention. The kit preferably is packaged in a container including a top cover 70 and a bottom cover 72, where the bottom cover 72 can include various compartments to house the respective components of the kit. The kit preferably includes above-described components such as the elongated flexible lead body 12, flexible guiding sheath 22, and stylet 20.

It will be understood by those of ordinary skill in the art that the subject invention encompasses other embodiments. For example, the fixation screw 32 may have a conical shape or another shape wherein its outer diameter varies longitudinally.

The described approaches and lead configurations will allow a physician to permanently map the threshold during lead placement while turning and extending the screw and inserting the lead epicardially into the myocardium. The pacing threshold can be measured, for example, by a temporary pacing system analyzer. Once the measured threshold values are acceptable, the physician can stop extending the screw.

Although the disclosed apparatus and method have been described with respect to preferred embodiments, it is apparent that modifications and changes can be made thereto without departing from the spirit and scope of the invention as defined by the appended claims.

What is claimed is:

1. A bipolar cardiac lead, comprising:
an elongated lead body having opposed proximal and distal end portions, and defining a longitudinal axis;
an electrode housing operatively associated with the distal end portion of the lead body for stimulating cardiac tissue;
a conductor coil extending through a lumen in the elongated lead body, the conductor coil being electrically connected to at least a connective portion of the electrode housing;
a helical fixation screw disposed within the electrode housing along an axis extending generally perpendicular to the longitudinal axis of the lead body and mounted for movement between an axially retracted position and an axially extended position for affixing the electrode housing to the cardiac tissue, wherein the helical fixation screw is electrically connected to the connective portion of the electrode housing; and
an insulating tube positioned radially outside of the helical fixation screw in the electrode housing for eluting at least one drug.

2. The bipolar cardiac lead as recited in claim 1, further including an internally threaded collar and an externally threaded plug disposed within the electrode housing, wherein the helical fixation screw depends from the externally threaded plug supported within the internally threaded collar.

3. The bipolar cardiac lead as recited in claim 2, further including a screwdriver tipped stylet extended into the electrode housing and a self-sealing opening formed in the electrode housing, wherein the externally threaded plug is configured for engagement with the screwdriver tipped stylet extended into the electrode housing through the self-sealing opening.

4. The bipolar cardiac lead as recited in claim 3, wherein the screwdriver tipped stylet is positioned outside the lead body.

5. The bipolar cardiac lead as recited in claim 3, further including a flexible guiding sheath positioned outside the lead body to accommodate the screwdriver tipped stylet.

6. The bipolar cardiac lead as recited in claim 5, wherein the guiding sheath has at least one bendable section.

7. The bipolar cardiac lead as recited in claim 1, wherein the electrode housing includes a ring electrode.

8. The bipolar cardiac lead as recited in claim 7, wherein the insulating tube is coaxially disposed within the ring electrode.

9. The bipolar cardiac lead as recited in claim 8, wherein the insulating tube is formed from a compound including an elastomer and a medicament.

10. The bipolar cardiac lead as recited in claim 9, wherein the compound from which the insulating tube is formed includes silicone and a steroid.

11. The bipolar cardiac lead as recited in claim 10, wherein the compound from which the insulating tube is formed has a durometer of about 40 to 90 Shore A.

12. The bipolar cardiac lead as recited in claim 10, wherein the compound from which the insulating tube is formed includes about 15% to 25% by weight steroid.

13. The bipolar cardiac lead as recited in claim 7, wherein the ring electrode is adapted to serve as an anode and a tip portion of the helical fixation screw is adapted to serve as a cathode.

14. The bipolar cardiac lead as recited in claim 7, wherein the ring electrode and a proximal portion of the helical fixation screw is adapted to serve as an anode, and a tip portion of the helical fixation screw is adapted to serve as a cathode.

15. The bipolar cardiac load as recited in claim 14, wherein the helical fixation screw further includes an insulator separating the proximal portion from the tip portion of the helical fixation screw.

16. The bipolar cardiac lead as recited in claim 1, wherein in the axially extended position, the helical fixation screw is adapted to penetrate into heart tissue a length of up to about to 10 mm.

17. The bipolar cardiac lead as recited in claim 1, wherein in the axially extended position, the helical fixation screw is adapted to penetrate into heart tissue a length of about 3 mm to 10 mm.

18. The bipolar cardiac lead as recited in claim 1, further including a needle-shaped fixation pin positioned within the helical fixation screw.

19. The bipolar cardiac lead as recited in claim 18, wherein the length of the helical fixation screw is about 7 mm to 10 mm, and the length of the fixation pin is about 5 mm to 7 mm.

20. The bipolar cardiac lead as recited in claim 1, wherein the lead body contains at least one conductor coil.

21. The bipolar cardiac lead as recited in claim 20, further including an insulating sheath of biocompatible material covering the at least one conductor coil.

22. The bipolar cardiac lead as recited in claim 1, further including a connector operatively associated with the proximal end of the lead body.

23. A bipolar cardiac lead, comprising:
an elongated lead body having opposed proximal and distal end portions, and defining a longitudinal axis;
an electrode housing operatively associated with the distal end portion of the lead body, the electrode housing including a ring electrode for stimulating cardiac tissue;
a helical fixation screw disposed within the electrode housing along an axis extending generally perpendicular to the longitudinal axis of the lead body and mounted for movement between an axially retracted position and an axially extended position for affixing the electrode housing to the cardiac tissue, wherein the helical fixation screw depends from an externally threaded plug supported within an internally threaded collar disposed within the electrode housing;
an insulating tube positioned radially outside of the helical fixation screw in the electrode housing for eluting at least one drug; and a screwdriver tipped stylet extended into the electrode housing and configured for engagement with the externally threaded plug.

24. The bipolar cardiac lead as recited in claim 23, wherein the screwdriver tipped stylet is positioned outside the lead body.

25. The bipolar cardiac lead as recited in claim 23, further including a flexible guiding sheath positioned outside the lead body to accommodate the screwdriver tipped stylet.

26. The bipolar cardiac lead as recited in claim 23, wherein the insulating tube is coaxially disposed within the ring electrode.

27. The bipolar cardiac lead as recited in claim 26, wherein the insulating tube is formed from a compound comprising an elastomer and a medicament.

28. The bipolar cardiac lead as recited in claim 27, wherein the compound from which the insulating tube is formed includes silicone and a steroid.

29. The bipolar cardiac lead as recited in claim 28, wherein the compound from which the insulating tube is formed has a durometer of about 40 to 90 Shore A.

30. The bipolar cardiac lead as recited in claim 28, wherein the compound from which the insulating tube is formed includes about 15% to 25% by weight steroid.

31. The bipolar cardiac lead as recited in claim 23, wherein the helical fixation screw includes a proximal portion and a distal portion terminating in a tip portion.

32. The bipolar cardiac lead as recited in claim 31, wherein the ring electrode is adapted to serve as an anode and the tip portion of the helical fixation screw is adapted to serve as a cathode.

33. The bipolar cardiac lead as recited in claim 31, wherein the ring electrode and the proximal portion of the helical fixation screw are adapted to serve as an anode, and the tip portion is adapted to serve as a cathode.

34. The bipolar cardiac lead as recited in claim 33, wherein the helical fixation screw further includes an insulator separating the proximal portion from the tip portion of the helical fixation screw.

35. The bipolar cardiac lead as recited in claim 23, wherein a self-sealing opening is formed in the electrode housing for receiving the screwdriver tipped stylet.

36. A cardiac lead implantation kit, comprising:
a bipolar cardiac lead including:

an elongated lead body having opposed proximal and distal end portions, and defining a longitudinal axis;

an electrode housing operatively associated with the distal end portion of the lead body for stimulating cardiac tissue;

a helical fixation screw disposed within the electrode housing along an axis extending generally perpendicular to the longitudinal axis of the lead body and mounted for movement between an axially retracted position and an axially extended position for affixing the electrode housing to the cardiac tissue; and an insulating tube positioned radially outside of this helical fixation screw in the electrode housing for eluting at least one drug;

a screwdriver tipped stylet for facilitating movement of the helical fixation screw; and a flexible guide sheath for directing the tip of the stylet to the electrode housing.

37. The cardiac lead implantation kit as recited in claim 36, wherein a self-sealing opening is formed in the electrode housing for receiving the screwdriver tipped stylet.

38. The cardiac lead implantation kit as recited in claim 37, wherein the electrode housing includes a ring electrode.

39. The cardiac lead implantation kit as recited in claim 38, further including an insulating tube coaxially disposed within the ring electrode.

40. The cardiac lead implantation kit as recited in claim 39, wherein the insulating tube is formed from a compound comprising an elastomer and a medicament.

41. The cardiac lead implantation kit as recited in claim 40, wherein the compound from which the insulating tube is formed includes silicone and a steroid.

42. The cardiac lead implantation kit as recited in claim 41, wherein the compound from which the insulating tube is formed has a durometer of about 40 to 90 Shore A.

43. The cardiac lead implantation kit as recited in claim 41, wherein the compound from which the insulating tube is formed includes about 15% to 25% by weight steroid.

44. The cardiac lead implantation kit as recited in claim 37, wherein the ring electrode is adapted to serve as an anode and a tip portion or the helical fixation screw is adapted to serve as a cathode.

45. The cardiac lead implantation kit as recited in claim 44, wherein the helical fixation screw further includes an insulator separating the ring electrode from the tip portion of the helical fixation screw.

46. The cardiac lead implantation kit as recited in claim 37, wherein the ring electrode and a proximal portion of the helical fixation screw are adapted to serve as an anode, and a tip portion of the helical fixation screw is adapted to serve as a cathode.

47. The cardiac lead implantation kit as recited in claim 46, wherein the helical fixation screw further includes an insulator separating the proximal portion from the tip portion of the helical fixation screw.

* * * * *